(12) United States Patent
Baid

(10) Patent No.: US 10,335,579 B2
(45) Date of Patent: Jul. 2, 2019

(54) INTRAVENOUS CATHETER APPARATUS

(71) Applicant: POLY MEDICURE LIMITED, Faridabad, Haryana (IN)

(72) Inventor: Rishi Baid, New Dehli (IN)

(73) Assignee: POLY MEDICURE LIMITED, Faridabad, Haryana (IN)

(*) Notice: Subject to any disclaimer, the term of this patent is extended or adjusted under 35 U.S.C. 154(b) by 55 days.

(21) Appl. No.: 15/022,458

(22) PCT Filed: Feb. 3, 2016

(86) PCT No.: PCT/IB2016/050536
§ 371 (c)(1),
(2) Date: Mar. 16, 2016

(87) PCT Pub. No.: WO2017/001942
PCT Pub. Date: Jan. 5, 2017

(65) Prior Publication Data
US 2017/0197062 A1    Jul. 13, 2017

(30) Foreign Application Priority Data
Jun. 27, 2015  (IN) .......................... 1916/DEL/2015

(51) Int. Cl.
*A61M 25/06* (2006.01)
*A61M 25/00* (2006.01)

(52) U.S. Cl.
CPC .... *A61M 25/0618* (2013.01); *A61M 25/0097* (2013.01); *A61M 25/0606* (2013.01); *A61M 25/0637* (2013.01)

(58) Field of Classification Search
CPC .............. A61M 25/0097; A61M 25/06; A61M 25/0606; A61M 25/0612; A61M 25/0618; A61M 25/0631; A61M 25/0637
See application file for complete search history.

(56) References Cited

U.S. PATENT DOCUMENTS 7,736,339 B2 * 6/2010 Woehr .............. A61M 25/0618
                                                  604/110
7,828,774 B2 * 11/2010 Harding ............ A61M 25/0618
                                                  604/164.07
(Continued)

FOREIGN PATENT DOCUMENTS

EP       1803477 A2    7/2007
WO    2013190407 A1   12/2013

OTHER PUBLICATIONS

Written Opinion for International Patent Application No. PCT/IB2016/050536 dated Apr. 5, 2016.
(Continued)

*Primary Examiner* — Quynh-Nhu H. Vu
(74) *Attorney, Agent, or Firm* — Moore & Van Allen PLLC; Henry B. Ward, III

(57) ABSTRACT

An intravenous catheter apparatus (10) comprising: a catheter tube (14); a catheter hub (12) having a distal end (22) and a proximal end (24), wherein the distal end (24) is joined to the catheter tube (14) and the proximal end (24) defines a housing (48); a needle (20) extending through the catheter hub (12) and the catheter tube (14) and defining an axial direction (A), wherein the needle (20) has opposite proximal and distal ends, the distal end forming a needle tip; a needle hub (16) attached to the proximal end of the needle (20); a needle guard (26) slidably arranged on the needle (20), wherein the needle guard (26) is movably retained in the housing (48) of the catheter hub (12), when the needle (20) extends through the catheter hub (12) and the catheter tube (14), wherein the needle guard (26) is removable from the catheter hub (12) once the needle tip is received in the needle guard (26) upon withdrawal of the needle (20) from the catheter tube (14), and wherein the housing (48) defines a chamber (54) at one end thereof ensuring that a first and second arm (40, 42) of the needle guard (26) do not engage (Continued)

or interact with an inner surface (56) of the chamber (54) prior and during venipuncture of a patient.

6 Claims, 3 Drawing Sheets

(56) References Cited

U.S. PATENT DOCUMENTS

| | | | |
|---|---|---|---|
| 2008/0249478 A1* | 10/2008 | Ishikura | A61M 25/0618 604/198 |
| 2009/0281499 A1* | 11/2009 | Harding | A61M 25/0618 604/164.08 |
| 2009/0312711 A1* | 12/2009 | Brimhall | A61M 25/0618 604/164.08 |
| 2013/0046315 A1* | 2/2013 | Woehr | A61M 25/0618 606/108 |
| 2014/0221939 A1* | 8/2014 | Woehr | A61M 5/158 604/263 |
| 2015/0151085 A1* | 6/2015 | Tan | A61M 25/0618 604/164.08 |
| 2015/0306349 A1* | 10/2015 | Bonnal | A61M 25/0097 604/272 |

OTHER PUBLICATIONS

International Search Report for for International Patent Application No. PCT/IB2016/050536 dated Apr. 5, 2016.

\* cited by examiner

INTRAVENOUS CATHETER APPARATUS

FIELD OF THE INVENTION

The invention generally relates to an intravenous catheter apparatus. More particularly, the invention relates to an intravenous catheter apparatus comprising a catheter hub arranged at a proximal end of a catheter tube and having an inner surface defining a housing; a needle having a needle tip and extending through the housing and the catheter tube when in a ready position; and a needle guard slidably arranged on the needle and received in the housing when the needle is in its ready position, wherein the needle guard is configured to guard the needle tip upon withdrawal of the needle from the catheter hub.

BACKGROUND OF THE INVENTION

An intravenous catheter apparatus of this kind is generally known. The needle guard serves to prevent a person handling the intravenous catheter apparatus from accidentally coming into contact with the needle tip after placement of the catheter tube in and subsequent removal of the needle from a patient's vein. Thereby, the intravenous catheter apparatus helps to avoid unwanted transmission of blood borne diseases.

Generally, when the needle is withdrawn from a patient, the needle grates or otherwise causes friction or creates a drag as it slides/passes through a catheter, a catheter hub or through a needle guard creating drag or a withdrawal force.

It is desired to provide an intravenous catheter apparatus that significantly decreases the withdrawal force required and friction caused as a needle is withdrawn through a catheter hub being protected by a needle guard.

SUMMARY AND OBJECTS OF THE INVENTION

A primary object and advantage of the present invention is to provide an intravenous catheter apparatus that significantly decreases the withdrawal force required and friction caused as a needle is withdrawn through a catheter hub being protected by a needle guard.

Another object and advantage of the present invention is to provide an improved intravenous catheter apparatus which is inexpensive to manufacture, efficient, effective and simple in its construction and use.

Accordingly, the present invention relates to an intravenous catheter apparatus comprising: a catheter tube; a catheter hub having a distal section and a proximal section, wherein the distal section is joined to the catheter tube and the proximal section defines a housing; a needle extending through the catheter hub and the catheter tube and defining an axial direction, wherein the needle has opposite proximal and distal ends, the distal end forming a needle tip; a needle hub attached to the proximal end of the needle; a needle guard slidably arranged on the needle, wherein the needle guard is movably retained in the housing of the catheter hub when the needle extends through the catheter hub and the catheter tube, and wherein the needle guard is removable from the catheter hub once the needle tip is received in the needle guard upon withdrawal of the needle from the catheter tube; and wherein the housing defines a chamber at one end thereof ensuring that a first and second arms of the needle guard do not engage or interact with an inner surface of the chamber prior and during venipuncture of a patient.

As well known in the art, the needle may have a needle feature close to its needle tip, which interacts with a proportional base of the needle guard, e.g. a curving or a bulge or any other change in profile. Thereby, it can be prevented that the needle is retracted out of the needle guard, which is known in the art.

In an embodiment, the catheter hub is made of two parts, a first part having a distal end section and a second part having a proximal end section. The first and second parts define the housing to receive the needle guard which is movably arranged on the needle shaft.

The chamber may be formed by an indentation in the housing for accommodating the first and second arm such that none of the arms deflected by the needle contacts an inner surface of the chamber. Through such indentation the overall outer dimensions of the housing and the catheter hub can be kept small, which it is still provided that the first and second arm of the needle guard do not contact the inner wall surface of the chamber.

Further, the first and second parts of the catheter hub may be joined by complementary end portions, which preferably as such extend at an angle with regard to the axial direction. This ensures that both parts are aligned concentrically towards each other. Thereby, the assembly of such a catheter hub can be made easier.

These end portions may be stepped, which enlarges their contact area for a better mutual interconnection.

The first and second part may form the chamber, in particular, the distal end section of the first part and the proximal end section of the second part may form the chamber, which ensures that no undercut has to be formed in either one of the first and second part.

The inner surface of the chamber may be parallel to the axial direction and defined only by one of the first or second part. Preferably the inner surface of the chamber is defined by either the distal end section of the first part or the proximal end section of the second part. More preferably the inner surface of the chamber is defined by the proximal end section of the second part. The advantage in this lies in the fact that only one of the two parts forming the catheter hub has to be dimensioned very precisely in order to ensure an inner surface with a well-controlled and large enough diameter such that none of the arms contact said inner surface. In this regard, it is advantageous that the inner surface of the chamber is defined by the second part comprising the fluid path 11. In this case only the second part requires more precise manufacturing while the first part can be manufactured without the necessity for tight tolerances.

The intravenous catheter apparatus according to one embodiment of the invention may be provided such that the other one of the first or second part comprises a surface joined with the inner surface of the one of the first or second part, which surface is inclined towards the inside of the housing in a proximal direction of the catheter hub, wherein the surface has a smaller inside diameter at its innermost end than a distance between outermost points of the arms in their deflected state inside the chamber. Preferably, the first part comprises the surface joined with the inner surface of the second part. Preferably, the distal end section of the first part comprises the surface joined with the inner surface of the proximal end section of the second part. Such a surface serves as a stop for the arms in their deflected state such that they cannot be pulled out of the catheter hub in the proximal axial direction as long as the needle deflects them outward in the ready position of the needle guard. On the other hand, the inclination of the surface supports that the arms are directed inwards when the needle guard is pulled out in the retracted position, even if they have been plastically deformed by the needle in their deflected state.

BRIEF DESCRIPTION OF THE ACCOMPANYING DRAWINGS

The foregoing and other objects, features, and advantages of the invention will be apparent from the following detailed description taken in conjunction with the accompanying drawings, wherein.

DETAILED DESCRIPTION OF THE INVENTION

Figure 1:
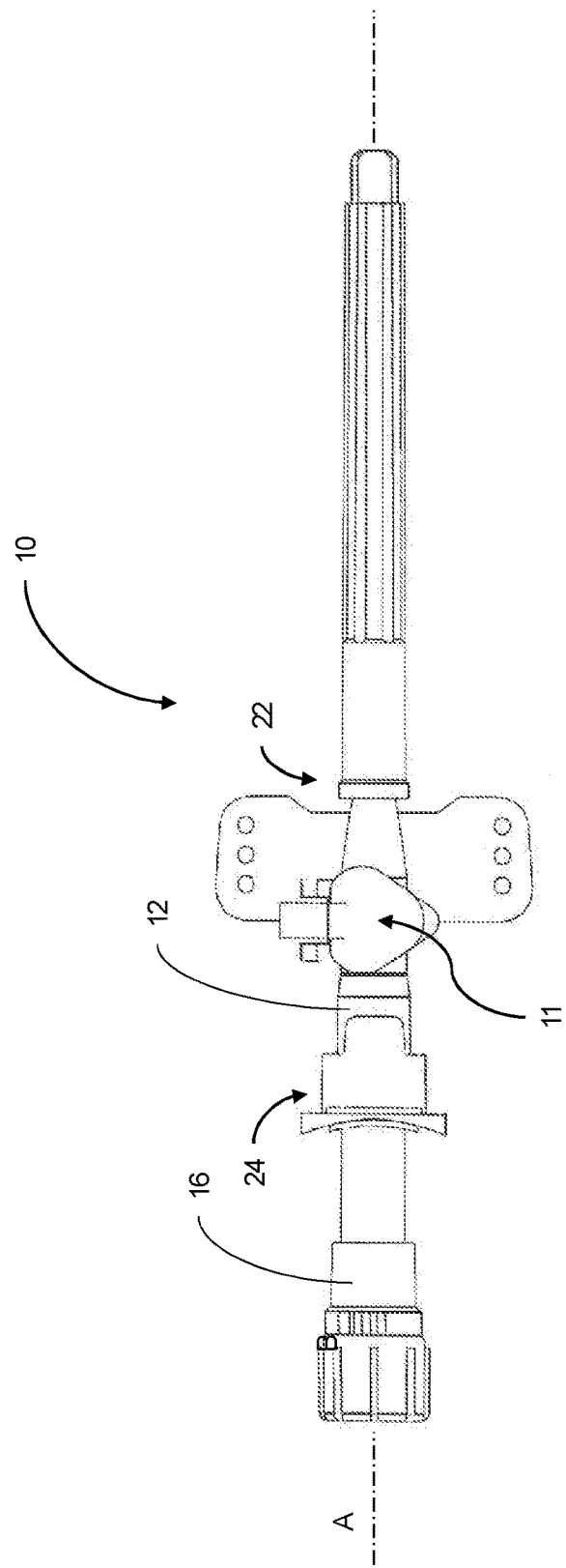
FIG. 1 is a top view of the intravenous catheter apparatus according to the present invention.

Embodiments of the presently disclosed invention will now be described in detail with reference to the drawings wherein like reference numerals designate identical or corresponding elements. In the drawings and in the description, the term "proximal" refers to a region of the device or parts thereof or a location on the device which is closest to, for example, a user using the device. In contrast to this, the term "distal" refers to a region of the device which is farthest from the user, for example, the distal region of a needle will be the region of the needle containing the needle tip which is to be inserted e.g. into a patient's vein.

Figure 2:
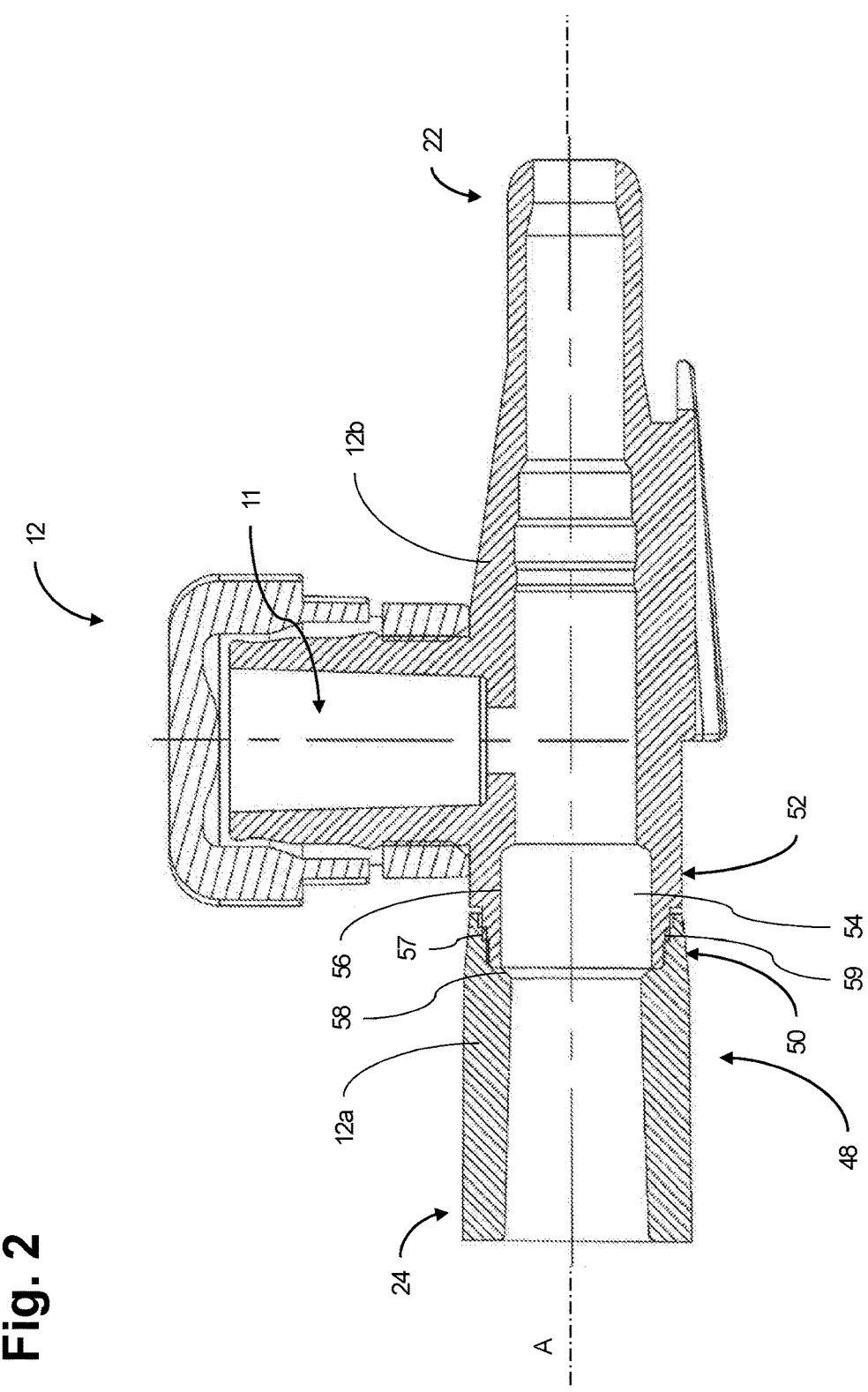
FIG. 2 is a cross-sectional side view of the two parts forming a catheter hub according to the present invention.
Figure 3:
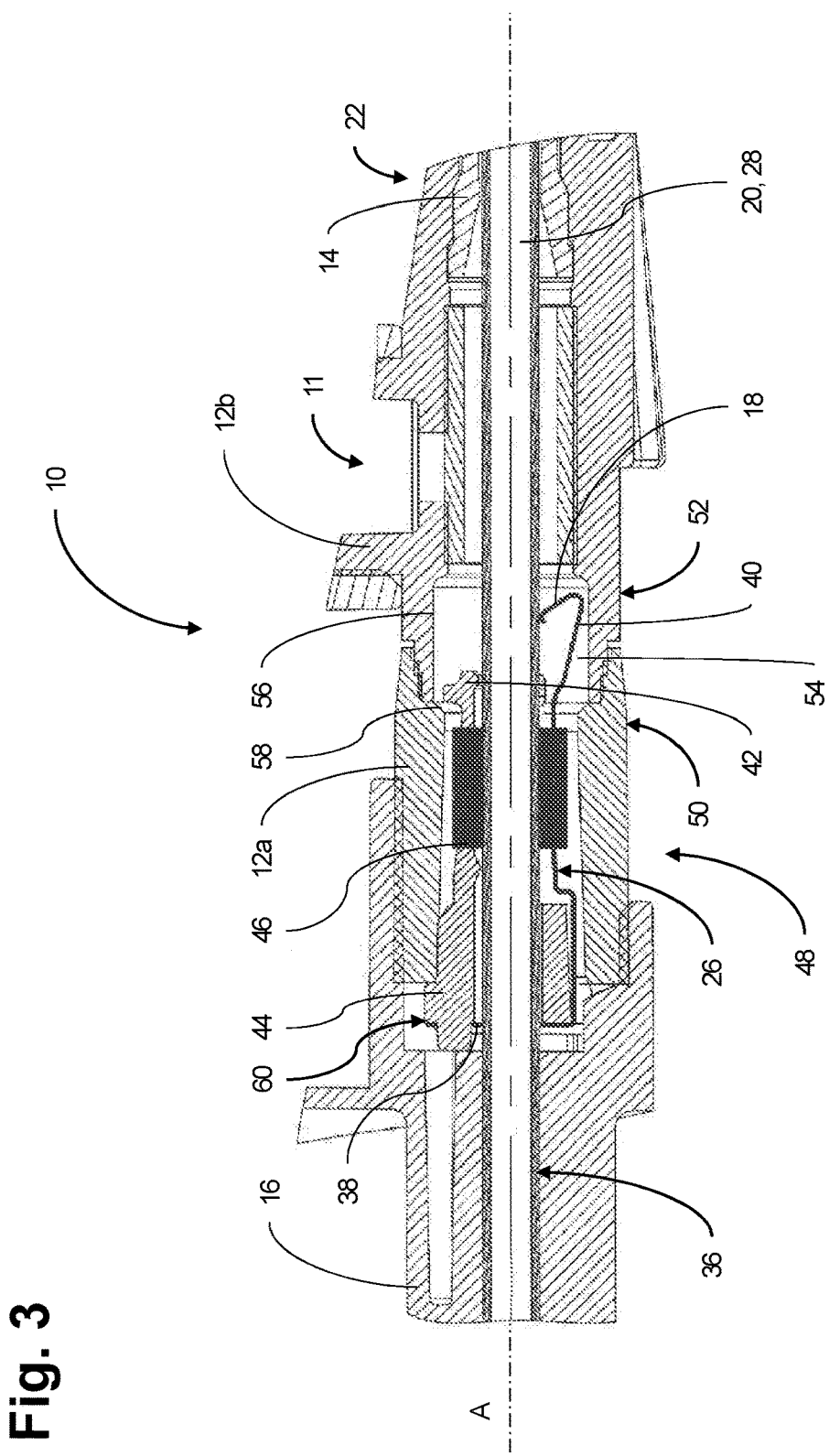
FIG. 3 is a cross-sectional side view of the two parts being joined together forming the catheter hub with a needle guard according to the present invention.

Referring to FIGS. 1-3 an intravenous catheter apparatus 10 in accordance with the invention is illustrated. The intravenous catheter apparatus 10 includes a catheter hub 12 having a fluid path 11, a catheter tube 14 and a needle 20. The catheter hub 12 has a distal end 22 and a proximal end 24, wherein the catheter tube 14 is arranged adjacent to the distal end 22 of the catheter hub 12. The needle 20 has a needle shaft 28, a needle tip at a distal section of the needle shaft 28 and a needle hub 16 attached to a proximal section 36 of the needle shaft 28. An enlargement (not shown) of the needle 20 is provided between the distal section and the proximal section 36 of the needle shaft 28. The enlargement has a maximum dimension in a direction transverse to the needle shaft 28, which is greater than the outer diameter of the distal or proximal section 36. The enlargement can be made, for example, by crimping the needle shaft 28.

Prior to use of the catheter apparatus 10, the needle 20 is received in the catheter hub 12 and catheter tube 14, such that the needle shaft 28 extends through the length of the catheter tube 14. A needle guard 26 is movably arranged on the needle shaft 28 and retained in the catheter hub 12 prior to use of the catheter apparatus 10 as shown in FIG. 3. The needle guard 26 has a base portion 44, a first arm 40, a second arm 42 and a distal wall 18. The distal wall 18 is arranged at a distal end of the first arm 40 and extends in a direction transverse to an axial direction A of the needle 20. A tension element 46, for example, a rubber band or the like, surrounds the first and second arms 40, 42. The first and second arms 40, 42 of the needle guard 26 extend generally in the axial direction A from a distal side 60 of the base portion 44, i.e. generally parallel to the needle shaft 28.

In one of the preferred embodiments, upon withdrawal of the needle 20 from the catheter tube 14 and catheter hub 12 the needle shaft 28 moves relative to the needle guard 26 until the needle tip is received in the needle guard 26. Once the needle tip is received in the needle guard 26 the enlargement of the needle shaft 28 engages with the base portion 44 of the needle guard 26 via a stopping element 38 such that the needle guard 26 can be pulled out of the catheter hub 12 together with the needle 20. An axial movement of the needle 20 relative to the needle guard 26 is now limited, as the distal wall 18 blocks the needle tip axially and the engagement between the enlargement and the base portion 44 via the stopping element 38 prevents the needle tip from being removed via the base portion 44, i.e. the needle tip is safely surrounded by the needle guard 26.

Referring now to FIG. 2, the catheter hub 12 is made of two parts, i.e. a first part 12a and a second part 12b comprising the fluid path 11. The first part 12a has a distal end section 50 and the second part 12b has a proximal end section 52. The first part 12a is part of a housing 48 to receive a needle guard 26 which is movably arranged on the needle shaft 28 of the needle 20. The distal end 22 of the second part 12b is connected to a catheter tube 14.

The distal end section 50 of the first part 12a is configured to be assembled with the proximal end section 52 of the second part 12b in various ways in a fluid tight manner, such as by adhesive sealing, ultrasonic welding, heated die, radio frequency sealing, mechanical seal (snap fit), insert molding, laser welding etc., ensuring a leak free joint. It is also possible to join the two parts 12a, 12b to one another, for example, using threads, interference, or snap-fit. In particular, as can be seen in FIGS. 2 and 3, the first and second parts 12a and 12b are joined by complementary stepped end portions As illustrated in FIGS. 2 and 3, the housing 48 is defined by the first and second parts 12a and 12b of the catheter hub 12 that houses the needle guard 26 and is configured such that it defines a chamber 54 at one end of the second part 12b. The chamber 54 is configured to provide room/space for the needle guard 26 in its ready position. The chamber 54 is formed by an indentation in the housing 48 for accommodating the first and second arms 40 and 42 such that none of the arms 40 and 42 deflected by the needle 20 contact the inner surface 56 of the chamber 54. In this embodiment, the chamber 54 is arranged in the proximal end section 52 of the second part 12b and defined by the first and second parts 12a and 12b, which are stuck together in axial direction by means of stepped surface areas 57, 59 of the two parts 12a, 12b.

In this ready position, the first arm 40 deflects outward of the needle guard 26 such that the distal wall 18 of the first arm 40 is supported on the needle shaft 28. Further, in this ready position, the first and second arms 40, 42 do not engage or interact with an inner wall/surface 56 of the chamber 54 prior and during venipuncture of a patient. The inner surface 56 is parallel to the axial direction A and defined only by the second part 12b. This non-contact of the first and second arms 40, 42 with the inner surface 56 of the chamber 54 significantly decreases the withdrawal force required and friction caused when a needle 20 is withdrawn through a catheter hub 12 being protected by a needle guard 26 after use. Moreover, the first part 12a comprises a surface 58 which is inclined towards the inside of the housing 48 in a proximal direction of the catheter hub 12. This chamfered surface 58 forms a radial shoulder and serves as an axial stop in the proximal direction of the catheter hub 12 for the arms 40, 42 in their ready position. The surface 58 has a smaller inside diameter at its innermost end than a distance between outermost points of the arms 40 and 42 in their deflected state inside the chamber 54. In other words, the arms 40, 42 cannot pass this surface 58 in the ready position, as shown in FIG. 3. However, in this retracted position, the arms 40, 42 have swung radially inwardly and can pass the chamfered surface 58.

As shown in FIGS. 2 and 3, prior to the use of the intravenous catheter apparatus 10, the needle guard 26 is arranged in the catheter hub 12 near a proximal end 24 of the needle shaft 28. In this situation, the needle 20 extends completely through the needle guard 26, thereby deflecting the first arm 40 of the needle guard 26 outwards, i.e. at an angle to the axial direction A, such that the distal wall 18 of the first arm 40 is supported on the needle shaft 28. Following the insertion of the catheter tube 14 into a patient, the needle 20 is withdrawn from the catheter tube 14 and the needle shaft 28 moves through the needle guard 26 while the needle guard 26 is retained in the catheter hub 12. Once the needle tip passes the transverse distal wall 18 of the needle guard 26, while being retracted, such that the needle shaft 28 no longer supports the distal wall 18, a restoring force of the tension element 46 and the first arm's 40 inherent elasticity ensure that the first arm 40 of the needle guard 26 is moved back into alignment with the axial direction A, so that the needle tip is blocked by being axially covered by the distal wall 18 of the needle guard 26, i.e. the needle tip is prevented from axially projecting out of the needle guard 26.

The catheter apparatus 10 is particularly inexpensive to manufacture if the base portion 44, the first and second arms 40, 42 are integrally made from a first material. The first material may, for example, be a plastic material. Thus the base portion 44, the first and second arms 40, 42 could be manufactured by injection molding.

Alternatively, the base portion 44, and one of the first and second arms 40, 42 could be integrally made from a first material, e.g. a plastic material, and the other one of the first and second arms 40, 42 could be made from a second material different from said first material. For example, said other one of the first and second arms 40, 42 could include a strip of material having spring-like properties, e.g. a strip of sheet metal, providing the above-mentioned inherent elasticity.

The construction and shape of the improved intravenous catheter apparatus 10 of the present disclosure provides a simple configuration. The simple design of the intravenous catheter apparatus 10 is advantageous in a clinical setting because it smoothens the whole catheterization process thereby reducing injury or discomfort to a patient. In addition, such design greatly reduces manufacturing costs and is efficient, effective and simple in its construction and use.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the spirit or scope of the invention as set forth in the claims.

Accordingly, it is not intended that the scope of the foregoing description be limited to the exact description set forth above, but rather that such description be construed as encompassing such features that reside in the present invention, including all the features and embodiments that would be treated as equivalents thereof by those skilled in the relevant art.

The scope of the present invention herein disclosed is not limited by the particular disclosed embodiments described above but determined only by a fair reading of the appended claims.

LIST OF REFERENCE NUMERALS 10 intravenous catheter apparatus
11 fluid path
12 catheter hub
12a first part of catheter hub
12b second part of catheter hub
14 catheter tube
16 needle hub
18 distal wall
20 needle
22 distal end
24 proximal end
26 needle guard
28 needle shaft
36 proximal section
38 stopping element
40 first arm
42 second arm
44 base portion
46 tension element
48 housing
50 distal end section
52 proximal end section
54 chamber
56 inner surface/wall
57 stepped surface of part 12a
58 inclined inner surface
59 stepped surface of part 12b
60 distal side
A axial direction

The invention claimed is:

1. An intravenous catheter apparatus comprising:
a catheter tube;
a catheter hub having a distal end and a proximal end, wherein the distal end is joined to the catheter tube and the proximal end defines a housing;
a needle extending through the catheter hub and the catheter tube and defining an axial direction, wherein the needle has opposite proximal and distal ends, the distal end forming a needle tip;
a needle hub attached to the proximal end of the needle;
a needle guard slidably arranged on the needle, wherein the needle guard is movably retained in the housing of the catheter hub, when the needle extends through the catheter hub and the catheter tube, wherein the needle guard is removable from the catheter hub once the needle tip is received in the needle guard upon withdrawal of the needle from the catheter tube, wherein the housing defines a chamber at one end thereof ensuring that a first and second arm of the needle guard do not engage or interact with an inner surface of the chamber prior and during venipuncture of a patient, wherein the catheter hub is made of two separate parts comprising a first part and a second part, wherein the first and second parts form the chamber, wherein the inner surface of the chamber is parallel to the axial direction and defined only by the second part, wherein the first part comprises a chamfered surface abutting the inner surface of the chamber, which chamfered surface is inclined towards the inside of the housing in a proximal direction of the catheter hub, and wherein the chamfered surface has a smaller inside diameter at its innermost end than a distance between outermost points of the arms in their deflected state inside the chamber.

2. The intravenous catheter apparatus as claimed in claim 1, wherein the chamber is formed by an indentation in the housing for accommodating the first and second arm such that none of the arms deflected by the needle contact the inner surface of the chamber.

3. The intravenous catheter apparatus as claimed in claim 1, wherein the first and second parts define the housing to receive the needle guard which is movably arranged on the needle.

4. The intravenous catheter apparatus as claimed in claim 1, wherein a distal end section of the first part is joined with a proximal end section of the second part in a fluid tight manner.

5. The intravenous catheter apparatus as claimed in claim 1, wherein the first and second parts are joined by complementary end portions.

6. The intravenous catheter apparatus as claimed in claim 5, wherein the end portions are stepped.

* * * * *